US008449505B2

(12) United States Patent
Lin Lee

(10) Patent No.: US 8,449,505 B2
(45) Date of Patent: May 28, 2013

(54) AUTOMATICALLY RETRACTABLE MEDICALLY SAFETY INJECTOR AND PLUNGER COMBINATION THEREOF

(75) Inventor: Lee Lin Lee, Taipei (TW)

(73) Assignee: Bencha International Group Inc., Tortola (VG)

( * ) Notice: Subject to any disclaimer, the term of this patent is extended or adjusted under 35 U.S.C. 154(b) by 207 days.

(21) Appl. No.: 12/208,774

(22) Filed: Sep. 11, 2008

(65) Prior Publication Data

US 2010/0063443 A1    Mar. 11, 2010

Related U.S. Application Data

(63) Continuation-in-part of application No. 11/600,755, filed on Nov. 17, 2006, now Pat. No. 7,674,241.

(51) Int. Cl.
    *A61M 5/315*    (2006.01)
    *A61M 5/00*     (2006.01)

(52) U.S. Cl.
    USPC .......................................... 604/229; 604/110

(58) Field of Classification Search
    USPC .......................................... 604/110, 11, 229
    See application file for complete search history.

(56) References Cited

U.S. PATENT DOCUMENTS

| 6,086,568 A | 7/2000 | Caizza | |
| 6,494,863 B1 * | 12/2002 | Shaw et al. | 604/110 |
| 6,585,690 B1 * | 7/2003 | Hoeck et al. | 604/110 |
| 6,752,782 B2 * | 6/2004 | Liao | 604/110 |
| 6,872,193 B2 * | 3/2005 | Shaw et al. | 604/164.07 |
| 2003/0149403 A1 * | 8/2003 | Barker et al. | 604/198 |
| 2003/0212366 A1 * | 11/2003 | Bang | 604/196 |
| 2007/0185458 A1 * | 8/2007 | Lin Lee | 604/197 |

FOREIGN PATENT DOCUMENTS

EP    1192967 A1    4/2002

* cited by examiner

*Primary Examiner* — Nicholas Lucchesi
*Assistant Examiner* — Rebecca E Eisenberg
(74) *Attorney, Agent, or Firm* — Ming Chow; Sinorica, LLC

(57) ABSTRACT

A medically safety injector comprises a needle hub attached by a needle, a hollow barrel for engaging with the needle hub and guiding the needle hub to retract into the hollow barrel, and a plunger combination settled in the hollow barrel. The plunger combination comprises a retractable plunger and a hollow shank partially telescoped with the retractable plunger, wherein at least one raised portion is formed on an outer wall of the retractable plunger and at a telescoping portion for engaging at least one depression formed on an inner wall of the hollow shank so that when the plunger combination continuously receives a pushing force after the medically safety injector is used to perform the injection operation, the retractable plunger can smoothly retract into the hollow shank. Consequently, space in the hollow barrel originally occupied by the retractable plunger or hollow shank is freed for accommodating the retracted needle hub.

13 Claims, 14 Drawing Sheets

AUTOMATICALLY RETRACTABLE MEDICALLY SAFETY INJECTOR AND PLUNGER COMBINATION THEREOF

CROSS-REFERENCE TO RELATED APPLICATION

This application is a Continuation in-part of U.S. patent application Ser. No. 11/600,755 entitled "SAFE MEDICAL-DRUG INJECTOR AND COLLAPSIBLE PLUNGER COMBINATION THEREOF" filed on Nov. 17, 2006 now U.S. Pat. No. 7,674,241. The U.S. patent application Ser. No. 11/600,755 is incorporated herein as a reference.

BACKGROUND OF THE INVENTION

1. Technical Field

The present invention relates to safe injectors and, more particularly, to an automatically retractable medically safety injector and a plunger combination which is one-hand operatable and functions for automatically retracting a needle thereof after the needle is used.

2. Description of Related Art

For purposes of avoiding the risk of cross-infection of infectious disease such as AIDS, Hepatitis B, and Hepatitis C; precluding drug addicts from repeatedly using injectors; and protecting medical staff from being accidentally injured by used needles; most injectors used for conventional medical-drug injection operation are of a not-reusable safe design, namely disposable syringes, which are immediately destroyed after a single time of use. However, such disposable syringe is designed for facilitating a user to exert a force thereon during injection operation in a way that the syringe requires holding at a specific angle with the user's both hands. Consequently, for a diabetic who may have difficult to simultaneously use his/her both hands to operate the syringe to inject himself/herself with Insulin, he/she can only use a common syringe instead of a safe syringe, leading to an increased risk of infectious diseases.

With attempts to mend the aforementioned problem, Taiwan Patent 520995, which is entitled as "Automatically Retractable Medically Safety Injector" and U.S. Pat. No. 6,712,793 B1, which is entitled as "Needle Guard Assembly for the Needle of A Syringe Body", each suggests a novel and one-hand operatable safe syringe. As shown in FIGS. 1A and 1B, the syringe of prior arts comprises a hollow barrel 12', a needle hub 11' for engaging a needle 10', an annular retracting spring 13' and a breakable retracting plunger 14'. Therein, the breakable retracting plunger 14' including a proximal part 17', a breakable connection 18', and a hollow distal part 19', which are formed integrally as one piece. After the breakable retracting plunger 14' is assembled into the hollow barrel 12' and used to perform liquid-drug injection operation by a user, the user can continue pushing the breakable retracting plunger 14' toward the needle 10' to break the breakable connection 18', so that the proximal part 17' can retract into the hollow distal part 19'. As a result, space in the hollow barrel 12' can be partially spared such that the needle hub 11' can lead the used needle 10' to be accommodated in the hollow barrel 12' together.

However, to facilitate users' exerting force and ensure practicability of the above-mentioned breakable retracting plunger, there are strict requests for symmetry and precision of the breakable connection of the plunger. Consequently, the dimensional tolerance for the molds used to form the one-piece plunger through injection molding process is very small. Besides, the conventional plunger is liable to be broken during fabrication and transportation. Therefore, the yield rate and output are significantly limited while the costs of molds are unavoidably high. Further, with the precise design, safety function of retraction of such conventional plunger can only be effective when the plunger is operated at a predetermined force-exerting angle. Thus, when the prior syringe is implemented to inject a patient at his/her curved-contour skin portion or his/her delicate apparatus, such as the head, postauricular, eyes, or oral skin, it is difficult for a medical staff member to operate the syringe with his/her single hand. Moreover, clumsy operation due to the limited force-exerting angle can accidentally damage the syringe and cause discomfort to the patient.

SUMMARY OF THE INVENTION

The present invention has been accomplished under these circumstances in view. It is one objective of the present invention to provide a medically safety injector and a plunger combination thereof which facilitate one-hand operation and eliminate the liability to being damaged during injection operation by a user's inexact force-exerting angle and posture.

It is another objective of the present invention to provide a medically safety injector and a plunger combination thereof which eliminate the liability to being damaged during fabrication, for purposes of enhancing the quality and yields rate, improving the reliability, and reducing material waste and processing costs of the disclosed subject matter.

It is another objective of the present invention to provide a medically safety injector and a plunger combination thereof which can be easily made through plastic injection molding process, so as to ease the dimensional request for the precision of the molds for producing injectors and rationalize the dimensional tolerance, such that the manufacturing costs of the disclosed subject matter can be reduced.

It is another objective of the present invention to provide a medically safety injector and a plunger combination thereof which have functions of buffing received force and resisting transverse shear, in order to provide enhanced convenience to a user's injection operation and decrease failure rate of injection operation as well as patient pain.

It is yet another objective of the present invention to provide a medically safety injector and a plunger combination thereof which can be molded with increased output of single batch so as to significantly enhance the output of the disclosed subject matter.

It is still another objective of the present invention to provide a medically safety injector and a plunger combination thereof wherein a plunger thereof is made with present mechanical strength and desirable practicability so as to facilitate retracting a used needle thereof.

To achieve these and other objectives of the present invention, the automatically retractable medically safety injector and the plunger combination thereof are disclosed for single use of muscle injection, hypodermic injection or intravenous injection with liquid medical drug or blood drawing.

The medically safety injector comprises a needle hub attached with a needle, a hollow barrel engaging with the needle hub and guiding the needle hub to retract into the hollow barrel after the medically safety injector is used to perform an injection operation, and a plunger combination settled in the hollow barrel. The plunger combination includes a retractable plunger and a hollow shank partially telescoped with the retractable plunger. At least one raised portion is provided on an outer surface of the retractable plunger at a telescoping portion where the retractable plunger is partially telescoped with the hollow shank for wedging at least one depression formed on an inner surface of the hollow shank. Thereupon, when a user continues pushing the plunger combination after the injector is used for injection operation, the retractable plunger can retract into the hollow shank, so as to free space in the hollow barrel for accommodating the used needle hub.

According to one concept of the present invention, in the plunger combination of the medically safety injector, the hollow shank and the retractable plunger can be positionally exchanged. Particularly, to achieve optimal effect of retraction of the retractable plunger, the present invention discloses one or more transverse stress adjustable notches, which are positioned at a center of the retractable plunger and at the telescoping portion where the retractable plunger is partially telescoped with the hollow shank, and at least one stress adjustable notch, which is arranged on an inclined edge of the hollow shank and has a lengthwise depth not reaching the depression on the inner surface of the hollow shank.

The present invention further provides a reinforcing design for the retractable plunger and the hollow shank of the plunger combination of the present invention for harmonizing with force strength of one-hand operation and various force-exerting angles.

In a second embodiment of the present invention, an automatically retractable medically safety injector and a plunger combination thereof according to the present invention are provided with one or more exhausting opening formed on a lateral wall of the hollow shank and positioned distant from the telescoping portion, so that when the retractable plunger retracts into the hollow shank, the exhausting opening formed on the hollow shank properly functioning for exhausting air so as to avoid air drag hindering a pushing operation of a user's thumb and facilitate the user's injection operation. Similarly, when the retractable plunder of the plunger combination is positioned near a rear end of the hollow barrel, one or more exhausting opening may be formed on a lateral wall of the retractable plunder and positioned distant from the telescoping portion, so that desirable effect of air exhausting can be performed by the exhausting opening.

In a third and a fourth embodiments of the present invention, at least one transversely convex annular rib or one or more ranks of transversely convex dots, which are arranged adjacently or alternately, may be formed on the outer surface of the retractable plunger instead of the aforementioned raised portions. Correspondingly, at least one concave annular rib or one or more ranks of annular grooves, which are arranged adjacently or alternately, may be formed on the inner surface of the hollow shank instead of the aforementioned depressions.

Further, in a fifth embodiment of the present invention, at the telescoping portion of the retractable plunger and the hollow shank, a plurality of stoppers are formed on the lateral wall of the hollow shank adjacent to a lower edge of the retractable plunger and arranged along a direction where the retractable plunger retracts. Alternatively, a rough region is provided on the retractable plunger above the raised portions, as shown in a sixth embodiment, whereby an excessive pushing force from a user acting on the plunger can be neutralized or buffed, so that the retractable plunger can be prevented from prematurely retracting into the hollow shank before completion of injection operation and therefore successful injection operation can be ensured.

For improving yield rate and user practicability of the disclosed medically safety injector and the plunger combination thereof, an improved design is applied to the needle hub. As described in a seventh embodiment, a narrow barrel having a diameter smaller than that of the hollow barrel is integrally formed with the hollow barrel at a front end of the hollow barrel for accommodating a compressed spring and a portion of the needle hub so as to enhance the retraction of the needle hub. Therein, at least one hollow stopper (movable retaining ring) is provided around an opening of the hollow barrel where the hollow barrel borders on the narrow barrel, and an inner diameter of a hollow portion of the stopper is smaller than a diameter of part of the needle hub so as to prevent the needle hub from falling off outward when receiving an excessive pushing force during injection operation and to guide the needle hub to retract after injection operation is completed.

In addition to the hollow stopper, a neck portion disclosed by an eighth embodiment of the present invention is formed integrally with an opening of the narrow barrel while the hollow barrel is molded through injection molding process. The neck portion is formed with a through hole at a center thereof in a manner that only the needle and part of the needle hub are allowed to pass therethrough, whereby the needle hub can be also retained and a stretching length of the needle hub from the neck portion can be controlled for optimum retraction of the needle hub.

Instead of the integrally formed breakable connection used in the prior arts, a split design is applied to the automatically retractable medically safety injector and the plunger combination of the present invention. The retractable plunger and the hollow shank, which are made of a flexible material such as plastic or rubber, are separately produced by injection molding process and then assembled together. Thus, risks of accidentally damaging the plunger during fabrication and failed injection operation caused by the damaged plunger damaged before and during injection operation can be reduced. Besides, since the two-piece plunger can have components thereof separately molded and then assembled, required dimensional precision of molds can be lower than that of the one-piece plunger having the breakable connection wherein mechanical balance of the connected portion thereof has to be taken into consideration. As a result, design and manufacturing costs of the molds are reduced while the reliability and the quality stability of the products are enhanced.

On the other hand, the two-piece plunger combination surpasses the breakable connection used in the plunger of the prior syringe in mechanical balance property for resisting transverse shear. Therefore, when a patient uses his/her single hand to inject himself/herself, or when a medical staff member injects a patient at his/her body portion unfavorable to force exerting, the practicability of the disclosed subject matter is not deteriorated by the limitation of force-exerting angle or posture.

BRIEF DESCRIPTION OF THE DRAWINGS

The invention as well as a preferred mode of use, further objectives and advantages thereof, will best be understood by reference to the following detailed description of an illustrative embodiment when read in conjunction with the accompanying drawings, wherein.

DETAILED DESCRIPTION OF THE PREFERRED EMBODIMENT

Some particular embodiments of the invention will be described in detail for purpose of illustration, and one of ordinary skill in the art can easily understand the advantages and efficacy of the present invention through the disclosure of the specification. It is to be understood that alternative embodiments may be possible for the implement and application of the present invention while numerous variations will be possible to the details disclosed in the specification on the strength of diverse concepts and applications without going outside the scope of the invention as disclosed in the claims.

Figure 1A:
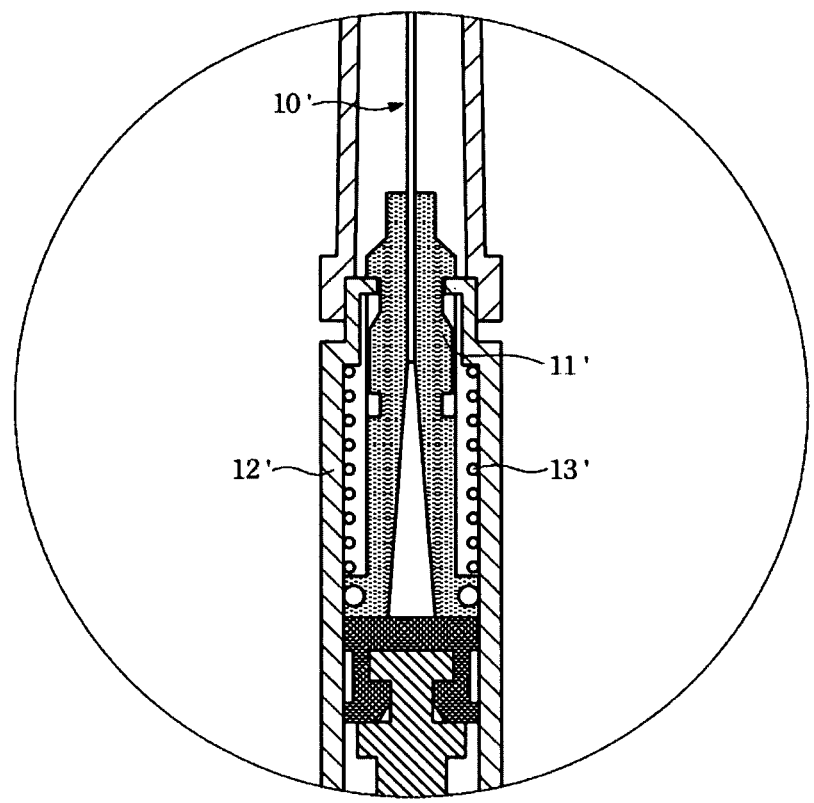
FIGS. 1A and 1B are a cross sectional view and a partial cross sectional view of a conventional automatically retractable medically safety injector.
Figure 1B:
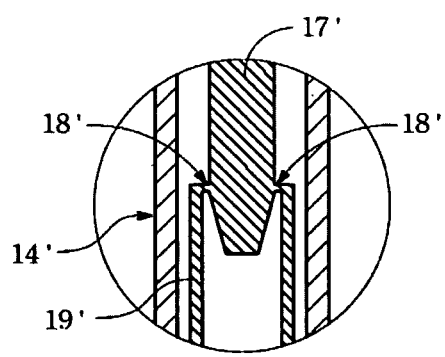
Figure 2:
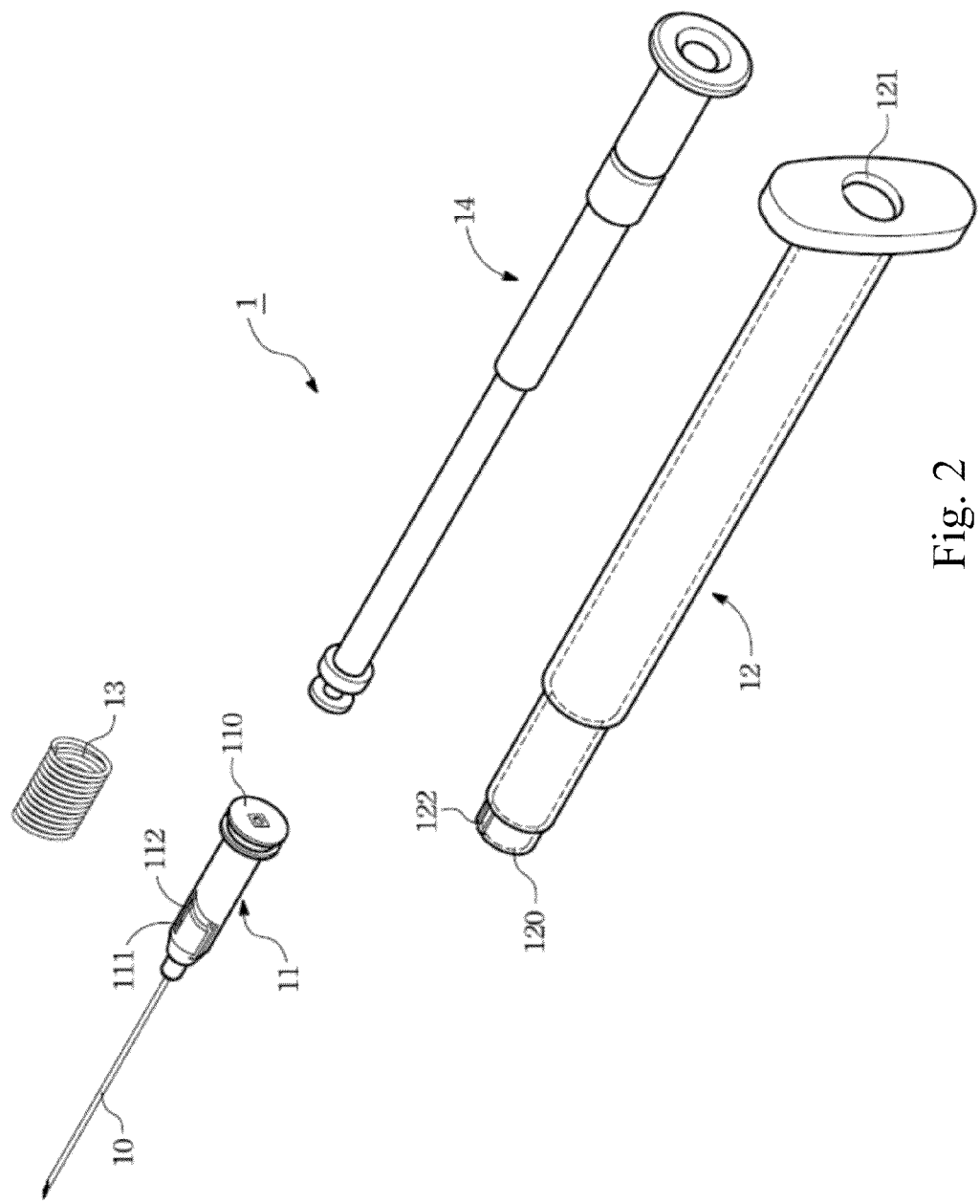
FIG. 2 is an extended view of a medically safety injector and a plunger combination according to a first embodiment of the present invention.
Figure 3A:
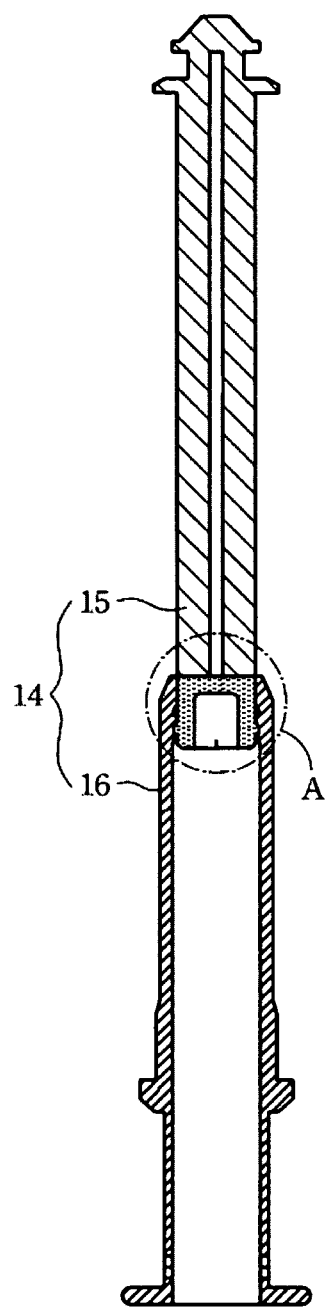
FIGS. 3A and 3B include a cross sectional view and a partial enlarged cross sectional view of the plunger combination according to the first embodiment of the present invention.
Figure 3B:
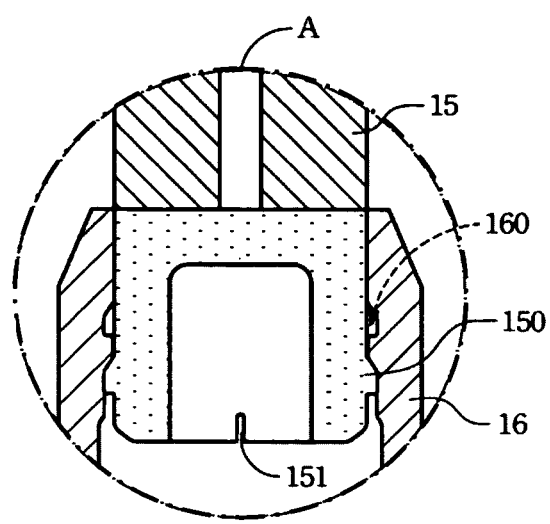
Figure 4:
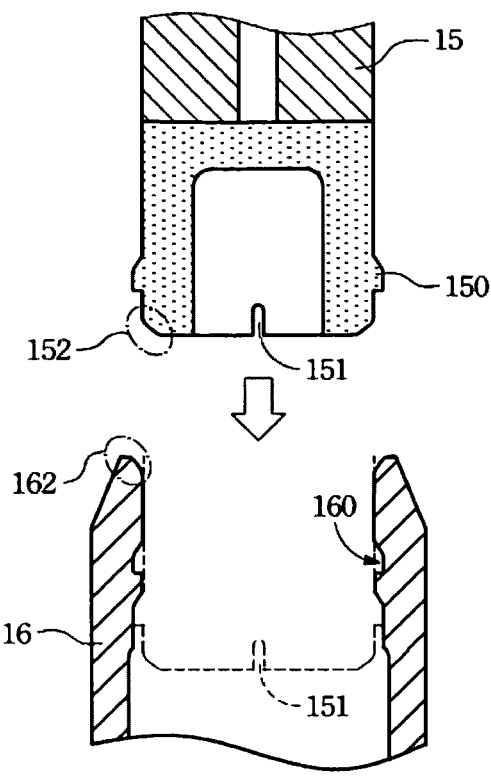
FIG. 4 is a schematic drawing showing a retractable plunger and a hollow shank of the plunger combination partially telescoped according to the first embodiment of the present invention.

FIGS. 2, 3, and 4 are respectively an extended view, cross sectional views and schematic drawing of an automatically retractable medically safety injector and a plunger combination thereof for single use of muscle injection, hypodermic injection or intravenous injection with liquid medical drug or blood drawing according to the present invention. It is to be noted that the recited drawings are simplified for conceptually illustrating the embodiments of the present invention. Components shown in the drawings are not necessarily the actual forms of the implement of the present invention. The numbers, shapes and dimensional scales of the components of the present invention may be embodied with a selective design and typically with a more complex arrangement.

Referring to FIG. 2, according to a first embodiment of the present invention, the disclosed automatically retractable medically safety injector 1 comprises at lease: a needle hub 11 attached with a needle 10, a hollow barrel 12, and a plunger combination 14 settled in the hollow barrel 12. The hollow barrel 12 engages with the needle hub 11 and at least one annular retracting spring 13 is implemented to guide the needle hub 11 to retract along a direction opposite to a direction where the needle hub moves during injection operation.

Particularly, the needle hub 11 has one end thereof accommodating the needle 10 that penetrates a center of the needle hub 11 and has an opposite end provided with a disc 110 for receiving the compressed annular retracting spring 13. Pluralities of positioning grooves 111 and U-shaped slide passages 112 contacting the positioning grooves 111 are disposed at proper positions between the two ends of the needle hub 11. The positioning grooves 111 are used to engage with a front end 120 of the hollow barrel 12 so that when the annular retracting spring 13 is released from a compressed position, the needle hub 11 is released from the front end 120 of the hollow barrel 12 and retracts along the U-shaped slide passages 112 toward the direction opposite to the direction where the needle hub moved during injection operation. By adjusting the U-shaped slide passages 112, a distance where the needle hub 11 retracts for can be controlled to prevent the needle 10 from jutting out the hollow barrel 12. However, any component that has elastic recovery property and can be compressed and released, such as a metal leaf spring, may be used as an equivalent substitute of the annular retracting spring 13.

Further, as shown in FIG. 2, the hollow barrel 12 has the front end 120 and a rear end 121. A plurality of elastic retaining hook 122, which are slightly flexible, are deposited at the front end 120 of the hollow barrel 12 in a manner that the elastic retaining hooks 122 face a center of the hollow barrel 12. When the disclosed subject matter is in an original state before being used and during injection operation, the elastic retaining hooks 122 firmly engage with the positioning grooves 111 of the needle hub 11. When a user continues pushing the plunger combination 14 toward the needle 10 after completion of injection operation, the elastic retaining hooks 122 are indirectly pressed and flexibly expanded so that the needle hub 11 can detach from the elastic retaining hooks 122 and retract into the hollow barrel 12.

Please refer to FIGS. 3A and 3B. According the first embodiment of the present invention, the disclosed automatically retractable medically safety injector 1 is characterized by a novel design of the plunger combination 14. As shown in the drawing, the plunger combination 14 has a two-piece structure and is composed of a retractable plunger 15 and a hollow shank 16, which are separately molded through injection molding process and then assembled together. Therein, a bottom of the retractable plunger 15 is placed inside the hollow shank 16. Further, as shown in FIG. 3B (i.e. a telescoping portion A of FIG. 3A), a plurality of raised portions 150 are formed an outer surface of the retractable plunger 15 while a plurality of depressions 160 are formed on an inner surface of the hollow shank 16 positionally corresponding to the raised portions 150. When the plunger combination 14 is in the original state before being used or during injection operation, the raised portions 150 of the retractable plunger 15 firmly engage with the depressions 160 of the hollow shank 16. When a user continues pushing the plunger combination 14 toward the needle 10 after completion of injection operation, the raised portions 150 are forced to depart from the depressions 160 so that the retractable plunger 15 can retract into the hollow shank 16, and space in the hollow barrel 12 originally occupied by the retractable plunger 15 is freed for accommodating the retracted needle hub 11 (as shown in FIG. 2).

Furthermore, the retractable plunger 15 or the hollow shank 16 depicted in FIG. 3A is made of a slightly flexible material, such as polyethylene (PE), polyvinyl chloride (PVC) or rubber, or a transparent rigid plastic, such as polypropylene (PP) or an AN series plastic and molded through injection molding process. In virtue of stiffness provided by the transparent rigid plastic, the retractable plunger 15 and the hollow shank 16 can bear desirable injecting force. According to the present embodiment, a trunk portion of the retractable plunger 15 can be shaped as a lengthwise cross rib or a column.

Referring to FIG. 3B, in order to maintain balancing of stresses on the plunger combination 14, the present embodiment provides a modified mode. That is, one or more transverse stress adjustable notches 151, which are positioned at a center of the retractable plunger 15 and at the telescoping portion A where the retractable plunger 15 and the hollow shank 16 are partially telescoped. The transverse stress adjustable notches 151 may be caves, blind holes or through holes. Generally, each of the transverse stress adjustable notches 151 has a lengthwise depth not approaching or reaching a position where the raised portions 150 are formed on the outer surface of the retractable plunger 15. Thereupon, when the plunger combination 14 is continuously pushed after completion of injection operation, the transverse stress adjustable notches 151 can become deformed so as to make the raised portions 150 detach from the depressions 160.

Furthermore, the raised portions 150 in the present embodiment may be a plurality of raised dots integrally formed on the retractable plunger 15 when the retractable plunger 15 is molded through injection molding process. Shapes, dimensions, amounts and arrangement of the raised dots are not to be limited by the present embodiment. However, in the present embodiment, six pairs of symmetrically arranged raised dots are implemented as a preferable embodying mode while a plurality of convex annular ribs may be also used as equivalent substitutes of the raised portions 150 described in the present embodiment.

Please refer to FIG. 4 for the structure of the hollow shank 16. To make the hollow shank 16 partially telescope and firmly engage with the retractable plunger 15, the plurality of depressions 160 are formed on the inner wall of the hollow shank 16 near where the hollow shank 16 partially telescopes the retractable plunger 15 for engaging the plurality of raised portions 150. The depressions 160 may be recesses, dents or partial or intact concave annular ribs and the depressions 160 may have C-shaped, chamfered rectangular, or irregular sectional shapes. Actually, depressions having any sectional shapes may be equivalent substitutes of the depressions 160 of the present embodiment, as long as the sectional shapes thereof can firmly engage with the raised portions 150 of the retractable plunger 15. However, in the present embodiment, intact concave annular ribs are implemented as a preferable embodying mode. Thereby, rotation of the retractable plunger 15 is not hindered by geometric positions of the raised portions 150 when the retractable plunger 15 is assembled to the hollow shank 16.

From FIG. 4, the retractable plunger 15 has a lower edge 152 thereof below the raised portions 150 chamfered while the hollow shank 16 has an upper edge 162 formed as a cambered, chamfered or inclined surface Therefore, an inner diameter of the upper edge 162 of the hollow shank 16 can be equal to or greater than an outer diameter of the lower edge 152 of the retractable plunger 15. Hence, when the raised portions 150 are detached from the depressions 160 after completion of injection operation, the retractable plunger 15 can slide into the hollow shank 16 and perform retraction smoothly.

Figure 5:
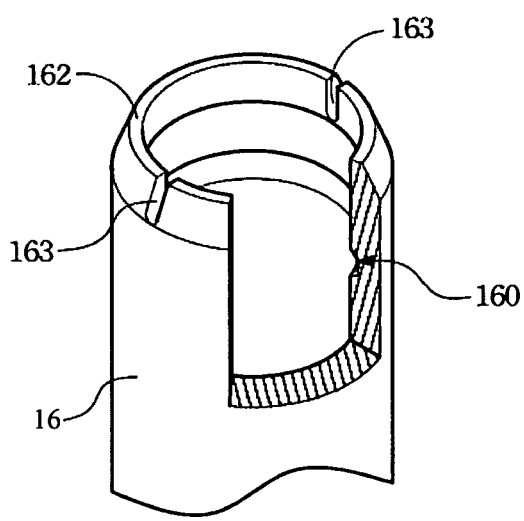
FIG. 5 is a perspective view of the hollow shank in the medically safety injector according to the first embodiment of the present invention.

When the plunger combination 14 is put into practical manufacture, strength of retracting and pulling forces of the retractable plunger 15 and the hollow shank 16 have to meet specific mechanical test standards. Thus, as shown in FIG. 5, the first embodiment of the present invention further discloses another modified mode, wherein at least one stress adjustable notch 163 is additionally formed on the inclined upper edge 162 of the hollow shank 16. The stress adjustable notch 163 has a lengthwise depth not reaching the depressions 160 on the inner surface of the hollow shank 16 and may be, for example, a cave or a blind hole.

According to the present invention, in the plunger combination 14 of the medically safety injector 1, the hollow shank 16 and the retractable plunger 15 can be positionally exchanged. No apparent limitation of relative position of the two components is made in the present embodiment. In addition to the arrangement that the retractable plunger 15 is positioned near the needle hub 11 so that a direction where the retractable plunger 15 retracts after completion of injection operation is coordinated to a direction where the needle hub 11 retracts after the needle hub 11 is detached, in an alternative embodiment as described below, the retractable plunger 15 is positioned at a rear portion of the hollow barrel 12 and distant from the needle hub 11.

Now please refer to FIG. 6A to 6D. A plunger combination 14 is a two-piece combination composed of a retractable plunger 15 and a hollow shank 16. A plurality of raised portions 150 are formed an outer surface of the retractable plunger 15 while a plurality of depressions 160 are formed on an inner surface of the hollow shank 16 positionally corresponding to the raised portions 150. When the plunger combination 14 is in an original state before being used or during injection operation, the raised portions 150 of the retractable plunger 15 firmly engage with the depressions 160 of the hollow shank 16. The difference between the present embodying mode and the aforesaid embodying mode is that the retractable plunger 15 and the hollow shank 16 are positionally exchanged. When a user continues pushing the plunger combination 14 toward the needle 10 after completion of injection operation, the raised portions 150 formed on a top portion of the inner wall of the retractable plunger 15 are forced to detach from the depressions 160 so that the retractable plunger 15 can retract into the hollow shank 16.

Figure 6A:
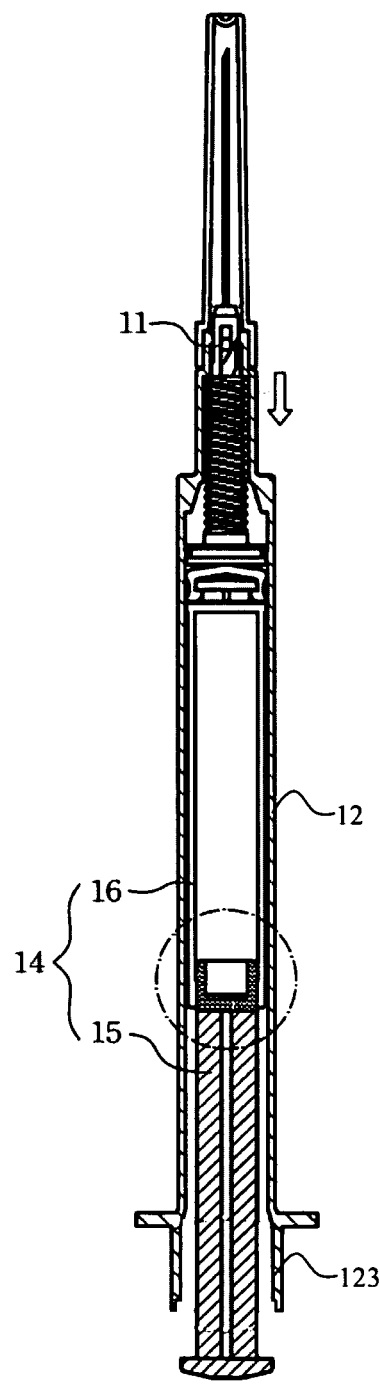
FIGS. 6A to 6D show an alternative embodying mode of the medically safety injector according to the first embodiment of the present invention.
Figure 6B:
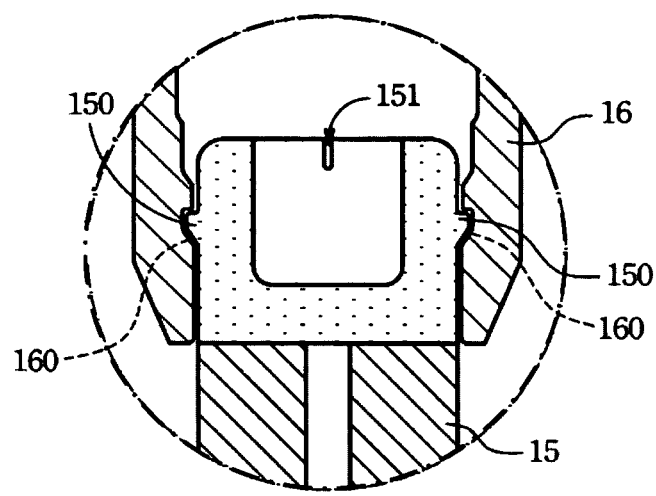
Figures 6C, 6D:
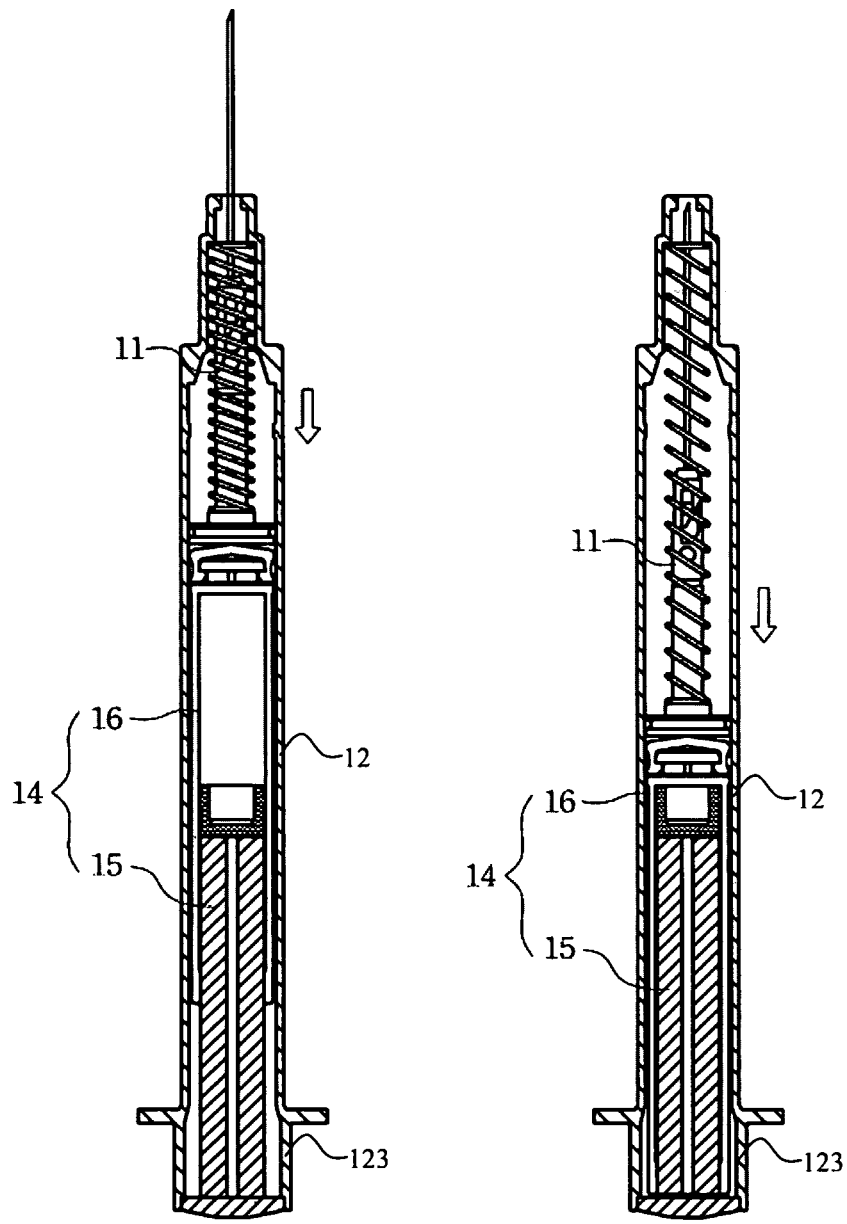

At this time, as shown in FIGS. 6C and 6D, a direction where the retractable plunger 15 retracts into the hollow shank 16 is opposite to a direction where the needle hub 11 retracts into the hollow barrel 12 after the raised portions 150 detach from the depressions 160. Even, to ensure the preferable practicability for one-hand operation of the plunger combination 14 having the retractable plunger 15 positioned at the rear portion of the hollow barrel 12, a plurality of extending portions 159 may be provided at a rear end of the hollow barrel 12 and two sides of a bottom of the retractable plunger 15 for controlling a distance where the retractable plunger 15 retracts for so as to spare sufficient space in the hollow barrel 12 for accommodating the needle hub 11.

Besides, a wing 123 is formed on the distant end of the hollow barrel 12 as depicted in FIG. 6A so as to prevent users from pushing the retractable plunger 15 too further and resulting in the destruction of the plunger combination 14. Such configuration could also be applied in the aforementioned embodying mode that the retractable plunger 15 is positioned near the needle hub 11.

All the details described above are preferable embodying modes of the first embodiment of the present invention and not to be regarded as limitations to the present invention. Any plunger combination is a two-piece combination composed of a hollow shank and a retractable plunger that are partially telescoped shall be considered as within the equivalent range of the present invention despite the modifications on sequence, combining means and segmental connection of the hollow shank and the retractable plunger. Meanwhile, the present invention further provides a reinforcing design for the retractable plunger and the hollow shank of the plunger combination for harmonizing with force strength of one-hand operation and various force-exerting angles.

FIGS. 7 through 14 illustrate alternative embodiments of the medically safety injector and the plunger combination thereof according to the present invention. While the alternative embodiments are different from the first embodiment with some particular components, the other components are substantially identical to those described in the first embodiment. Hence, the following descriptions will be only directed to the characteristics that distinguish the alternative embodiments from the first embodiment and those components identical to those described in the first embodiment will not be discussed at length.

Figure 7:
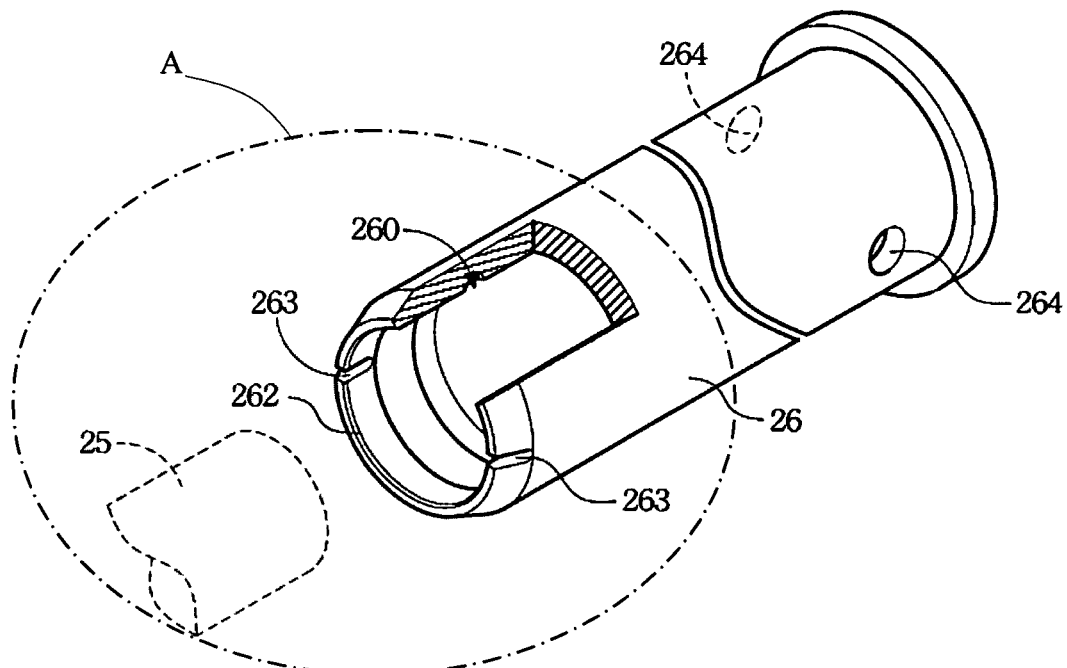
FIG. 7 is a partially sectioned perspective view of a hollow shank in a medically safety injector according to a second embodiment of the present invention.

FIG. 7 illustrates a second embodiment of a medically safety injector and a plunger combination thereof according to the present invention. As shown in the drawing, a hollow shank 26 of the plunger combination is provided with one or more exhausting opening 264 formed on a lateral wall of the hollow shank 26 and positioned distant from the telescoping portion as shown in FIGS. 3A, 3B and 6B. Thereupon, when a retractable plunger 25 retracts into the hollow shank 26, air drag can be eliminated through the exhausting opening 264 and does not hinder pushing operation of a user's thumb so as to facilitate the user's operation. In the present embodiment, a concave annular rib 260 is used instead of the depressions 160 used in the first embodiment while an upper edge 262 and stress adjustable notches 263 used herein are similar to the upper edge 162 and the stress adjustable notches 163 used in the first embodiment.

Figure 8:
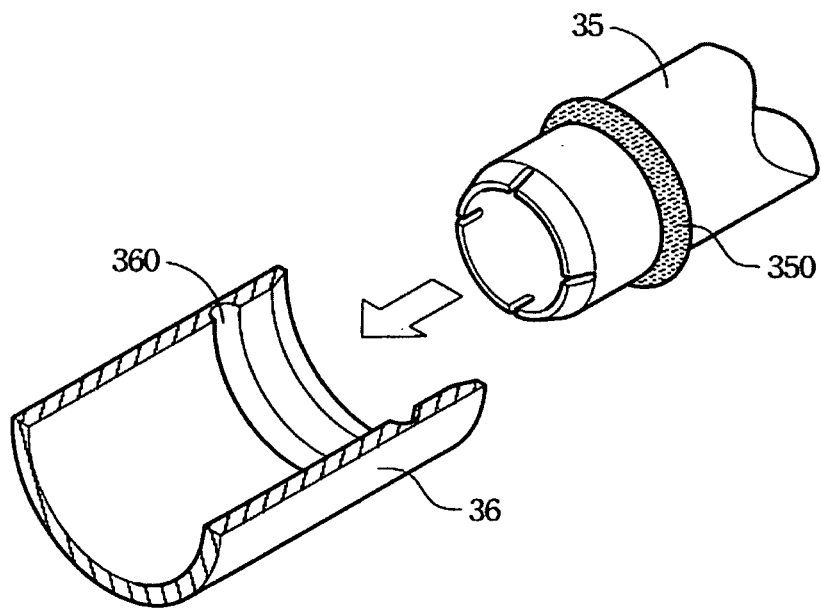
FIG. 8 is a partially sectioned perspective view of a plunger combination in a medically safety injector according to a third embodiment of the present invention.

Please refer to FIG. 8. In a third embodiment of a medically safety injector and a plunger combination thereof according to the present invention, a transversely convex annular rib 350 having a continuous or intermittent contour is formed on an outer of a retractable plunger 35 instead of the raised portions 150 of the first embodiment (as shown in FIGS. 3B and 6B). Meanwhile, a concave annular rib 360 having a continuous or intermittent contour or one or more ranks of annular grooves each having a continuous or intermittent contour are formed on the hollow shank 36 instead of the depressions 160 used in the first embodiment (as shown in FIGS. 3B and 6B). The convex annular rib 350 and the concave annular rib 360 may be provided in a form of a single rank, respectively, or may be in a form of multiple ranks, respectively, as disclosed by a forth embodiment of a medically safety injector and a plunger combination thereof according to the present invention, which is shown in FIG. 9.

Figure 9:
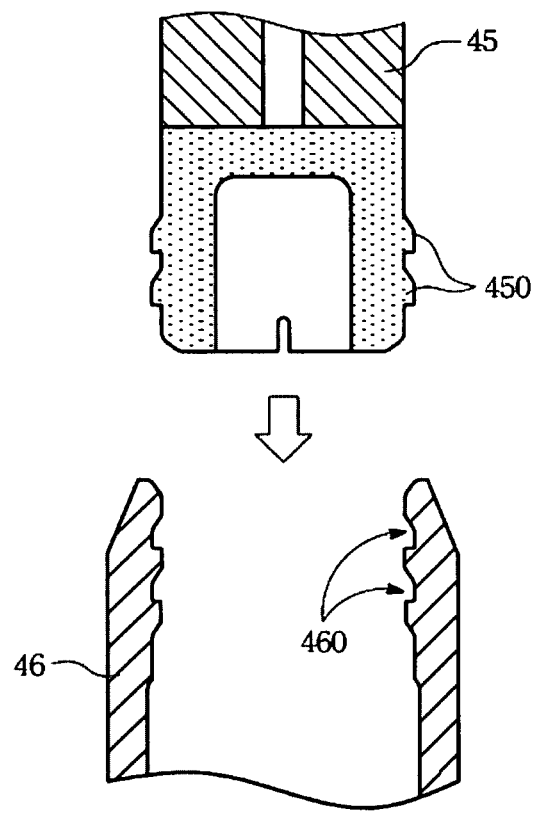
FIG. 9 is a partial cross sectional view of a plunger combination in a medically safety injector according to a fourth embodiment of the present invention.

According to the forth embodiment shown in FIG. 9, plural ranks of transversely convex annular ribs 450 each having a continuous or intermittent contour are arranged in a vertically adjacent or alternate manner on an outer surface of a retractable plunger 45 so as to replace the raised portions 150 of the first embodiment (as shown in FIGS. 3B and 6B). Correspondingly, plural ranks of concave annular ribs 460 each having a continuous or intermittent contour are arranged in a vertically adjacent or alternate manner on an inner surface of the hollow shank 46 so as to replace the depressions 160 used in the first embodiment (as shown in FIGS. 3B and 6B).

On the other hand, to make the retractable plunger of the plunger combination meet specific mechanical requests for strength of pulling and retracting forces, the present invention further provides an improvement structure below the above-mentioned depressions or concave annular ribs or annular grooves of the hollow shank.

Figure 10:
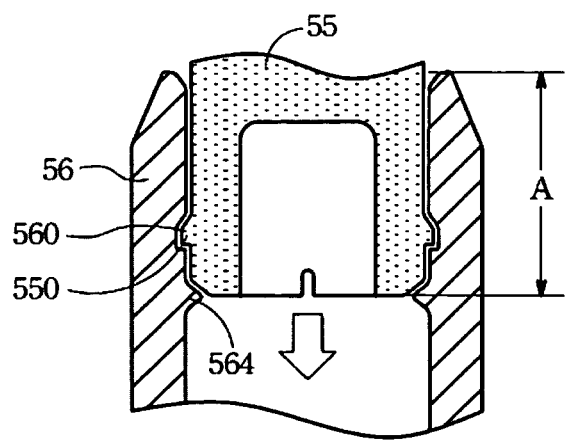
FIG. 10 is a partial cross sectional view of the plunger combination in a medically safety injector according to a fifth embodiment of the present invention.

In FIG. 10, a fifth embodiment of a medically safety injector and a plunger combination according to the present invention is illustrated. Therein, a plurality of stoppers 564 are formed at the telescoping portion A and near a lower edge of a depression or a concave annular rib or a annular groove 560 deposited on an inner wall of a hollow shank 56 along a direction where a retractable plunger 55 retracts. The stoppers 564 contribute to an enhanced counterforce of the retractable plunger 55 during injection operation so that the retractable plunger 55 and the hollow shank 56 can be combined with enhanced firmness. Therein, the stoppers 564 may be raised portions formed integrally with the hollow shank 56 through injection molding process or affixed blocks. Further, the stoppers 564 each having an extending surface perpendicular to a lengthwise axis of the hollow shank 56 or inclined along a direction coordinated to a direction where the retractable plunger 55 retracts.

Figure 11:
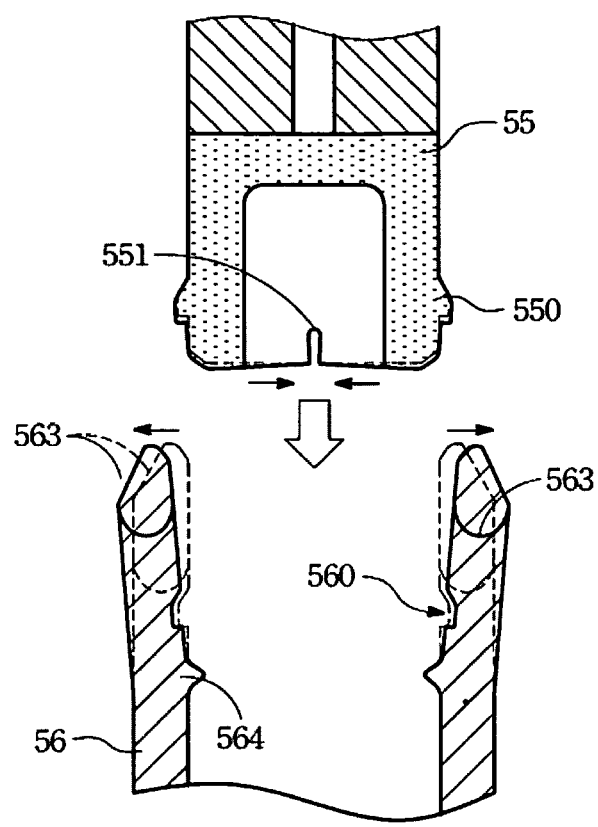
FIG. 11 is a schematic drawing showing in a medically safety injector, a retracting plunger retracting into a hollow shank according to the fifth embodiment of the present invention.

In the fifth embodiment, the stoppers 546 are designed as having the extending surfaces inclined along the direction coordinated to the direction where the retractable plunger 55 retracts. Thus, as shown in FIG. 11, when a user continues pushing the plunger combination after liquid drug is fully injected, the raised portions 550 of the retractable plunger 55 are transversely compressed toward a stress adjustable notch 551 to synchronously enter into the hollow shank 56. At this time, the downward inclined extending surface of the stoppers 564 can guide the retractable plunger 55 to slide downward smoothly. In addition, as the hollow shank 56 is made of the slightly flexible material, the user's pushing force acting on the plunger combination can make stress adjustable notches 563 provided on an upper edge of the hollow shank 56 fleetingly expanded in a transverse direction so that the retractable plunger 55 can retract into the hollow shank 56 easier.

Figure 12:
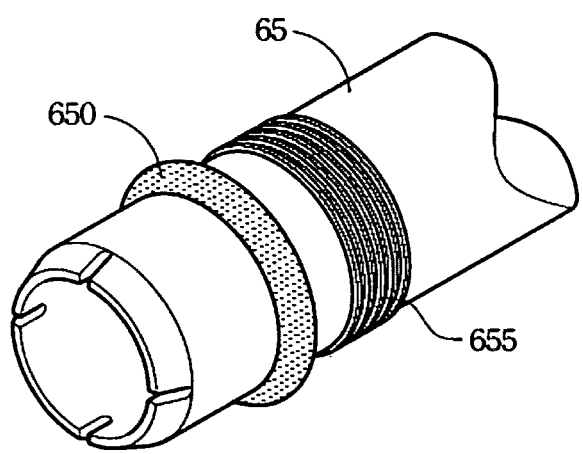
FIG. 12 is a perspective view of a retracting plunger having a rough region in a medically safety injector according to a sixth embodiment of the present invention.

FIG. 12 describes a sixth embodiment of a medically safety injector and a plunger combination according to the present invention. In the present embodiment, a rough region 655 constructed from, for example, uneven concave grooves and convex ribs, transverse striatures or rough surface with grains, is provided above a raised portion 650 on an outer surface of a retractable plunger 65. The rough region 655 functions for neutralizing or buffing a user's excessive pushing force acting on the plunger combination so as to prevent the retractable plunger 65 from prematurely retracting into the hollow shank (not shown) before completion of injection operation so that successful injection can be ensured.

The plunger combination of the automatically retractable medically safety injector disclosed in the present invention is designed as a two-piece structure. The retractable plunger and the hollow shank, which are made of a flexible material such as plastic or rubber, are separately molded through injection molding process and then assembled together. Thus, risks of accidentally damaging the plunger during fabrication and failed injection operation caused by the damaged plunger damaged before and during injection operation can be reduced. Besides, since the two-piece plunger can have components thereof separately molded and then assembled, required dimensional precision of molds can be lower than that of the one-piece plunger having the breakable connection wherein mechanical balance of the connected portion thereof has to be taken into consideration. As a result, design and manufacturing costs of the molds are reduced while the reliability and the quality stability of the products are enhanced.

On the other hand, the two-piece plunger combination surpasses the breakable connection used in the plunger of the prior syringe in mechanical balance property for resisting transverse shear. Therefore, when a patient uses his/her single hand to inject himself/herself, or when a medical staff member injects a patient at his/her body portion unfavorable to exerting force, the practicability of the disclosed medically safety injector and the plunger combination thereof will not be deteriorated because the limitations of force-exerting angle or posture are eliminated.

Figure 13:
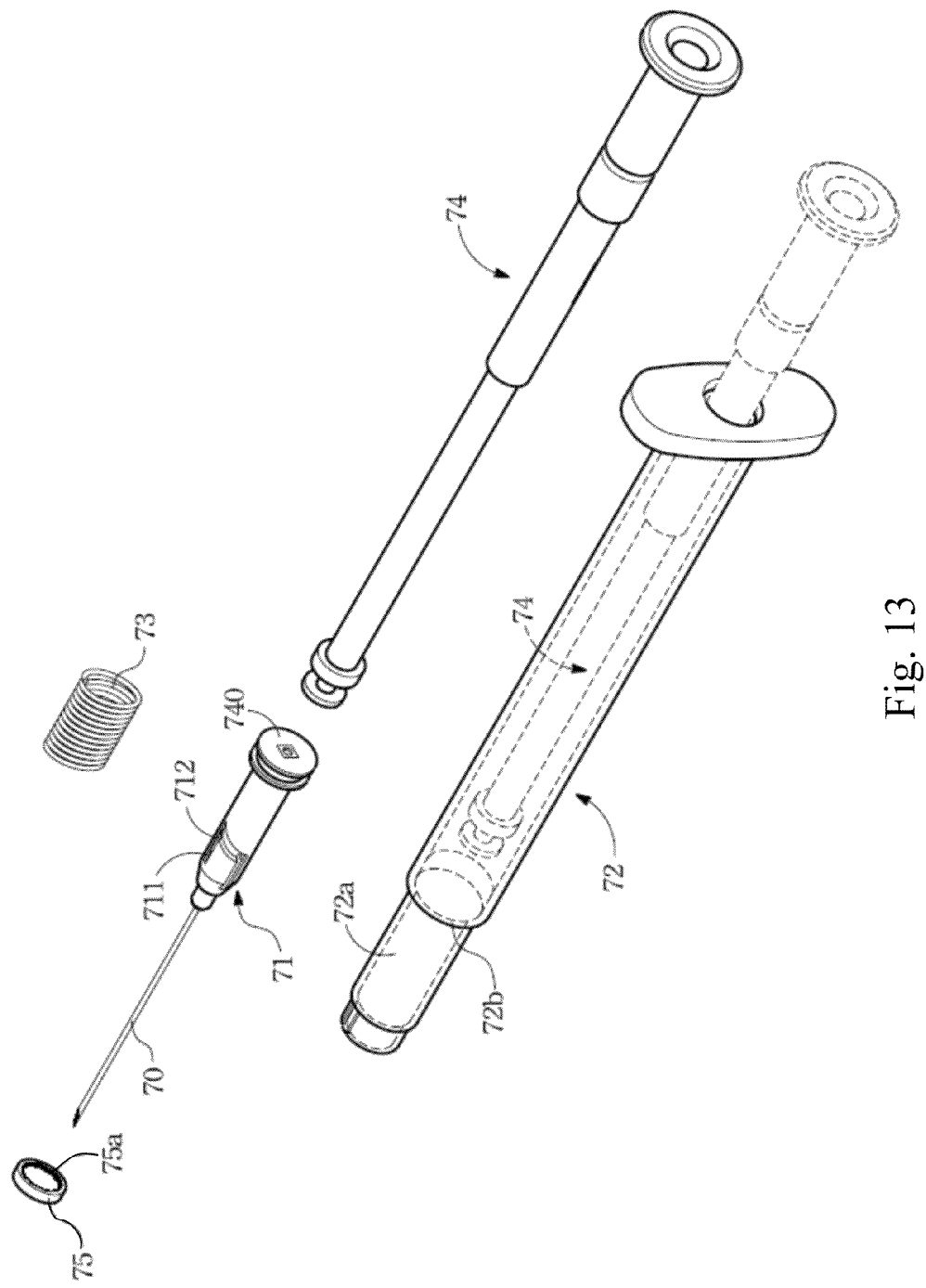
FIG. 13 is an exploded view of a medically safety injector according to a seventh embodiment of the present invention.
Figure 14A:
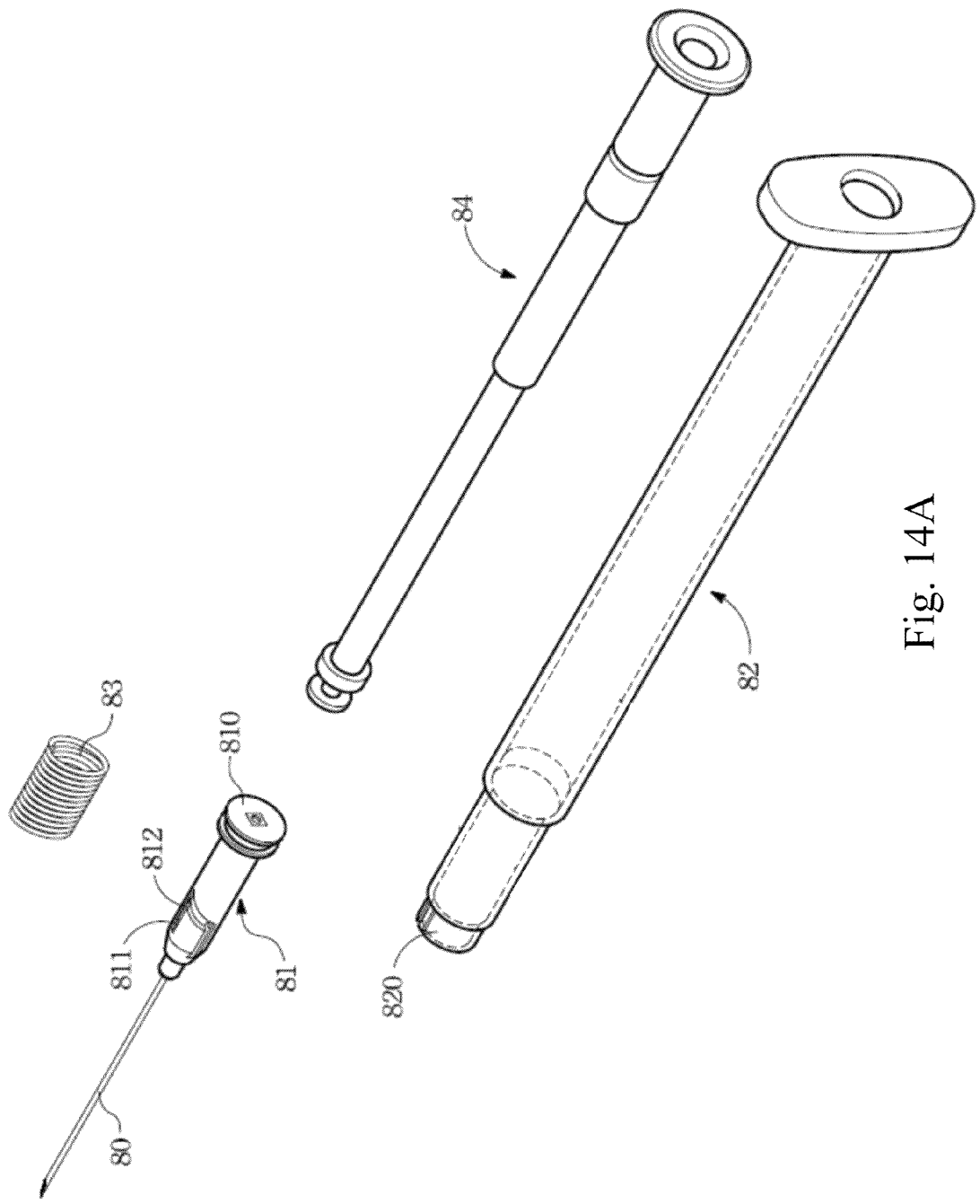
FIGS. 14A and 14B are an exploded view and a partial cross sectional view of a medically safety injector according to an eighth embodiment of the present invention.
Figure 14B:
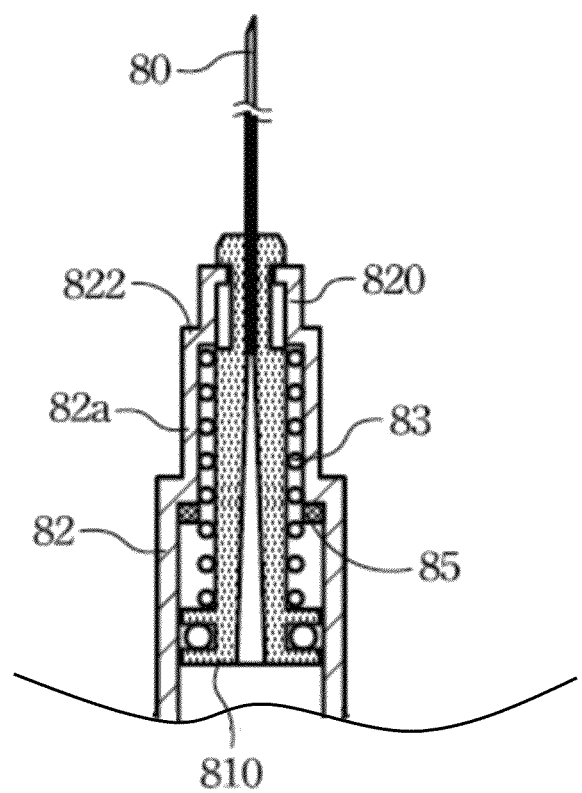

Especially, for improving the yield rate and user practicability of the disclosed medically safety injector and the plunger combination thereof, an improved design is applied to the needle hub. FIGS. 13 and 14 are provided to illustrate a seventh embodiment and an eighth embodiment of the present invention, respectively.

As shown in FIG. 13, for enhancing retraction of the needle hub, a narrow barrel 72*a* having a diameter smaller than that of the hollow barrel 72 is integrally formed with the hollow barrel 72 at a front end of the hollow barrel 72 for accommodating a annular retracting spring 73 and a front portion of the needle hub 71. Therein, at least one movable or stable stopper 75 is received around an opening 72*b* of the hollow barrel 72 where the hollow barrel 72 borders on the narrow barrel 72*a*, so as to prevent the needle hub 71 from falling off outward when receiving an excessive pushing force during injection operation and to guide the needle hub 71 to retract when injection operation is completed. A through hole 75*a* is provide at a center of the movable or stable stopper 75 for allowing the needle 70 and part of the needle hub 71 to pass therethrough. Further, the through hole 75*a* of the stopper 75 has an area smaller than that of a disc 710 of the needle hub 71 so that the needle hub 71 can be retained at a position for the optimum retraction. However, the movable or stable stopper may be one or more rings having an inner wall thereof formed as a smooth surface, or with regular or irregular arranged ratchets. In the present embodiment, a round ring having an inner wall of a through hole thereof formed with radial ratchets is used as a preferable embodying mode. The needle 70, the needle hub 71, positioning grooves 711, U-shaped slide passages 712, and an annular retracting spring 73 are respectively the same as the needle 10, the needle hub 11, the positioning grooves 111, the U-shaped slide passage 112, and the annular retracting spring 13 described in the first embodiment.

Besides, in the eighth embodiment, the present also discloses a neck portion 85 formed integrally with an opening of the hollow barrel 82 where the hollow barrel 82 borders on the narrow barrel 82*a* while the hollow barrel 82 is molded through injection molding process, as shown in FIG. 14, in addition to the movable or stable stopper 75 formed at the opening 72*b* of the narrow barrel 72*a*. A through hole is provide at a center of the neck portion 85, which has an area smaller than that of a disc 810, so that the disc 810 can be retained by the neck portion 85 and only allow a needle 80 and a front portion of a needle hub 81 to pass therethrough. Thereupon, the needle hub 81 can be also prevented from falling off outward. A plunger combination 84, an annular retracting spring 83, positioning grooves 811, U-shaped slide passages 812, and an elastic retaining hook 822 are respectively the same as the plunger combination 14, the annular retracting spring 13, the positioning grooves 111, the U-shaped slide passage 112, and the elastic retaining hook 122 described in the first embodiment. Although some particular embodiments of the invention have been described in detail for purposes of illustration, it will be understood by one of ordinary skill in the art that numerous variations will be possible to the disclosed embodiments without going outside the scope of the invention as disclosed in the claims.

What is claimed is:

1. A medically safety injector, comprising:
a needle hub having a first end and a second end with the first end being attached by a needle;
a hollow barrel for engaging with the needle hub and guiding the needle hub to retract into the hollow barrel after the medically safety injector is used to perform an injection operation; and
a collapsable plunger combination having a two-piece structure and settled in the hollow barrel, comprising a retractable plunger positioned near the second end of the needle hub rather than attached to the needle hub, and a hollow shank partially telescoped with the retractable plunger, wherein the retractable plunger and the hollow shank are separately molded through an injection molding process and then assembled together, at least one raised portion is formed on an outer wall of the retractable plunger at a telescoping portion, where the retractable plunger and the hollow shank are partially telescoped, for engaging at least one depression formed on an inner wall of the hollow shank, so that when the plunger combination continuously receives a pushing force after the medically safety injector is used to perform the injection operation, the raised portion detaches from the depression to force the retractable plunger to smoothly retract into the hollow shank so that space in the hollow barrel originally occupied by the retractable plunger is freed for accommodating the retracted needle hub, whereby the needle hub is retained in the hollow barrel rather than retracted into the collapsable plunger combination, after the completion of the injection operation.

2. The medically safety injector of claim 1, wherein the depression is one of one or more ranks of annular grooves arranged adjacently and one or more ranks of annular grooves arranged alternately.

3. The medically safety injector of claim 1, wherein a wing is formed on the distant end of the hollow barrel.

4. The medically safety injector of claim 3, wherein at least one exhausting opening is formed on a lateral wall of the hollow shank and positioned distant from the telescoping portion.

5. A medically safety injector, comprising:
a needle hub having a first end and a second end with the first end being attached by a needle;
a hollow barrel for engaging with the needle hub and guiding the needle hub to retract into the hollow barrel after the medically safety injector is used to perform an injection operation; and
a collapsable plunger combination having a two-piece structure and settled in the hollow barrel, comprising a hollow shank positioned near the second end of the needle hub rather than attached to the needle hub, and a retractable plunger partially telescoped with the hollow shank, wherein the retractable plunger and the hollow shank are separately molded through an injection molding process and then assembled together, at least one raised portion is formed on an outer wall of the retractable plunger at a telescoping portion, where the retractable plunger and the hollow shank are partially telescoped, for engaging at least one depression formed on an inner wall of the hollow shank, so that when the plunger combination continuously receives a pushing force after the medically safety injector is used to perform the injection operation, and in turn make the raised portion detach from the depression to force the retractable plunger to smoothly retract into the hollow shank so that space in the hollow barrel originally occupied by hollow shank is freed for accommodating the retracted needle hub, whereby the needle hub is retained in the hollow barrel rather than retracted into the collapsable plunger combination, after the completion of the injection operation.

6. The medically safety injector of claim 5, wherein the depression is one of one or more ranks of annular grooves arranged adjacently and one or more ranks of annular grooves arranged alternately.

7. The medically safety injector of claim 5, wherein a wing is formed on the distant end of the hollow barrel.

8. The medically safety injector of claim 7, wherein at least one exhausting opening is formed on a lateral wall of the hollow shank and positioned distant from the telescoping portion.

9. The medically safety injector of claim 5, wherein at least one stress adjustable notch is provided at an edge of the hollow shank and at the telescoping portion.

10. A plunger combination for a medically safety injector, the medical safety injector comprising:
   a needle hub attached by a needle;
   a hollow barrel for engaging with the needle hub and guiding the needle hub to retract into the hollow barrel after the medically safety injector is used to perform an injection operation;
   a plunger combination having a two-piece structure and settled in the hollow barrel and comprising,
   a retractable plunger; and
   a hollow shank partially telescoped with the retractable plunger, wherein the retractable plunger and the hollow shank are separately molded through an injection molding process and then assembled together, at least one raised portion is formed on an outer wall of the retractable plunger at a telescoping portion, where the retractable plunger and the hollow shank are partially telescoped, for engaging at least one depression formed on an inner wall of the hollow shank, so that when the plunger combination continuously receives a pushing force after the medically safety injector is used to perform an injection operation, the raised portion detaches from the depression to force at least one part of the retractable plunger to smoothly retract into the hollow shank so that space in the hollow barrel originally occupied by the retractable plunger or the hollow shank is freed for accommodating the retracted needle hub, whereby the needle hub is retained in the hollow barrel rather than retracted into the collapsable plunger combination, after the completion of the injection operation.

11. The plunger combination for the medically safety injector of claim 10, wherein the depression is one of one or more ranks of annular grooves arranged adjacently and one or more ranks of annular grooves arranged alternately.

12. The plunger combination for the medically safety injector of claim 10, wherein at least one stress adjustable notch is provided at a center of the retractable plunger and at the telescoping portion.

13. The plunger combination for the medically safety injector of claim 10, wherein at least one exhausting opening is formed on a lateral wall of the hollow shank and positioned distant from the telescoping portion.

* * * * *